(12) United States Patent
Scates et al.

(10) Patent No.: US 7,223,886 B2
(45) Date of Patent: *May 29, 2007

(54) REMOVAL OF PERMANGANATE REDUCING COMPOUNDS FROM METHANOL CARBONYLATION PROCESS STREAM

(75) Inventors: Mark O. Scates, Houston, TX (US); David A. Trueba, Webster, TX (US); Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/708,420

(22) Filed: Mar. 2, 2004

(65) Prior Publication Data

US 2005/0197508 A1     Sep. 8, 2005

(51) Int. Cl.
*C07C 51/10* (2006.01)
*C07C 51/42* (2006.01)
*C07C 45/78* (2006.01)

(52) U.S. Cl. .................. 562/608; 560/232; 562/519
(58) Field of Classification Search .................. None
See application file for complete search history.

(56) References Cited

U.S. PATENT DOCUMENTS

| | | | |
|---|---|---|---|
| 3,769,329 A | 10/1973 | Paulik et al. | 260/488 |
| 5,001,259 A | 3/1991 | Smith et al. | 562/519 |
| 5,026,908 A | 6/1991 | Smith et al. | 562/519 |
| 5,144,068 A | 9/1992 | Smith et al. | 562/519 |
| 5,416,237 A | 5/1995 | Aubigne et al. | 562/519 |
| 5,625,095 A | 4/1997 | Miura et al. | 562/519 |
| 5,723,660 A | 3/1998 | Morimoto et al. | 562/519 |
| 5,756,836 A | 5/1998 | Shimizu et al. | 562/519 |
| 5,783,731 A | 7/1998 | Fisher et al. | 562/519 |
| 6,143,930 A | 11/2000 | Singh et al. | 562/608 |
| 6,339,171 B1 | 1/2002 | Singh et al. | 562/519 |
| 2005/0197509 A1* | 9/2005 | Picard et al. | 562/608 |

FOREIGN PATENT DOCUMENTS

| | | |
|---|---|---|
| EP | 0 487 284 | 5/1992 |
| EP | 1 061 874 | 11/1995 |
| EP | 0 687 662 | 12/1995 |
| JP | 9-40590 | 2/1997 |

OTHER PUBLICATIONS

Neil T. Allison, Organic Chemistry Laboratory II, Chemistry 3712/3612, spring 2003 edition. Department of Chemistry and Biochemistry, University of Arkansas, p. 28.*

(Continued)

*Primary Examiner*—Joseph K. McKane
*Assistant Examiner*—Yevgeny Valenrod
(74) *Attorney, Agent, or Firm*—Howrey LLP

(57) ABSTRACT

An improvement of the methanol carbonylation process for manufacturing acetic acid is disclosed. Specifically disclosed is a method for reducing the formation of alkyl iodides and $C_{3-8}$ carboxylic acids by removing permanganate reducing compounds ("PRC's") from the light phase of the condensed light ends overhead stream, including (a) distilling the light phase to yield a PRC enriched overhead stream; and (b) extracting the third overhead stream with water in at least two consecutive stages and separating therefrom one or more aqueous streams containing PRC's.

7 Claims, 2 Drawing Sheets

OTHER PUBLICATIONS

Derrick J. Watson, *The Cativa Process for the Production of Acetic Acid*, *in* Catalysis of Organic Reactions, vol. 75, pp. 369-380 (1998).

R.T. Eby & T.C. Singleton, *Methanol Carbonylation to Acetic Acid*, *in* Applied Industrial Catalysis, vol. 1, pp. 275-296 (1983).

* cited by examiner

REMOVAL OF PERMANGANATE REDUCING COMPOUNDS FROM METHANOL CARBONYLATION PROCESS STREAM

BACKGROUND OF INVENTION

1. Field of the Invention

This invention relates to an improved process for the removal of permanganate reducing compounds and alkyl iodides formed by the carbonylation of methanol in the presence of a Group VIII metal carbonylation catalyst. More specifically, this invention relates to an improved process for reducing and/or removing precursors of permanganate reducing compounds and alkyl iodides from intermediate streams during the formation of acetic acid by said carbonylation processes.

2. Technical Background

Among currently employed processes for synthesizing acetic acid, one of the most useful commercially is the catalyzed carbonylation of methanol with carbon monoxide as taught in U.S. Pat. No. 3,769,329 issued to Paulik et al. on Oct. 30, 1973. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms, and the exact nature of the rhodium moiety within the active catalyst complex is uncertain. Likewise, the nature of the halide promoter is not critical. The patentees disclose a very large number of suitable promoters, most of which are organic iodides. Most typically and usefully, the reaction is conducted by continuously bubbling carbon monoxide gas through a liquid reaction medium in which the catalyst is dissolved.

An improvement in the prior art process for the carbonylation of an alcohol to produce the carboxylic acid having one carbon atom more than the alcohol in the presence of a rhodium catalyst is disclosed in commonly assigned U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; and European Patent No. EP 0 161 874 B2, published Jul. 1, 1992. As disclosed therein, acetic acid is produced from methanol in a reaction medium containing methyl acetate, methyl halide, especially methyl iodide, and rhodium present in a catalytically effective concentration. These patents disclose that catalyst stability and the productivity of the carbonylation reactor can be maintained at surprisingly high levels, even at very low water concentrations, i.e. 4 weight percent or less, in the reaction medium (despite the general industrial practice of maintaining approximately 14–15 wt % water) by maintaining in the reaction medium, along with a catalytically effective amount of rhodium and at least a finite concentration of water, a specified concentration of iodide ions over and above the iodide content which is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e. resistance to catalyst precipitation, especially during the product recovery steps of the process. In these steps, distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001, 259, 5,026,908 and 5,144,068 are herein incorporated by reference.

It has been found that although a low water carbonylation process for producing acetic acid reduces such by-products as carbon dioxide, hydrogen, and propionic acid, the amount of other impurities, present generally in trace amounts, is also increased, and the quality of acetic acid sometimes suffers when attempts are made to increase the production rate by improving catalysts, or modifying reaction conditions.

These trace impurities affect quality of acetic acid, especially when they are recirculated through the reaction process. The impurities that decrease the permanganate time of the acetic acid include carbonyl compounds and unsaturated carbonyl compounds. As used herein, the phrase "carbonyl" is intended to mean compounds that contain aldehyde or ketone functional groups, which compounds may or may not possess unsaturation. See *Catalysis of Organic Reaction,* 75, 369–380 (1998), for further discussion on impurities in a carbonylation process.

The present invention is directed to reducing and/or removing permanganate reducing compounds (PRC's) such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. The present invention also leads to reduction of propionic acid.

The carbonyl impurities described above, such as acetaldehyde, may react with iodide catalyst promoters to form multi-carbon alkyl iodides, e.g., ethyl iodide, propyl iodide, butyl iodide, pentyl iodide, hexyl iodide and the like. It is desirable to remove alkyl iodides from the reaction product because even small amounts of these impurities in the acetic acid product tend to poison the catalyst used in the production of vinyl acetate, the product most commonly produced from acetic acid. The present invention is thus also directed to removal of alkyl iodides, in particular $C_{2-12}$ alkyl iodide compounds. Accordingly, because many impurities originate with acetaldehyde, it is a primary objective to remove acetaldehyde from the process so as to reduce the alkyl iodide content.

Conventional techniques to remove impurities include treating the acetic acid product with oxidizers, ozone, water, methanol, activated-carbon, amines, and the like, which treatment may or may not be combined with distillation of the acetic acid. The most typical purification treatment involves a series of distillations of the final product. It is also known, for example from U.S. Pat. No. 5,783,731, to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Since a sufficient permanganate time is an important commercial test, which the acid product must meet to be suitable for many uses, the presence of impurities that decrease permanganate time is objectionable. Moreover, it is not economically or commercially feasible to remove minute quantities of these impurities from the acetic acid by distillation because some of the impurities have boiling points close to that of the acetic acid product.

It has thus become important to identify economically viable methods of removing impurities elsewhere in the carbonylation process without contaminating the final product or adding unnecessary costs. U.S. Pat. No. 5,756,836, incorporated herein by reference, discloses a method for manufacturing high purity acetic acid by adjusting the acetaldehyde concentration of the reaction solution below 1500 ppm. It is stated that by maintaining the acetaldehyde concentration below this threshold, it is possible to suppress the formation of impurities such that one need only distill the crude acetic acid product to obtain high purity acetic acid.

European Patent No. EP 0 487 284 B1, published Apr. 12, 1995, discloses that carbonyl impurities present in the acetic acid product generally concentrate in the overhead from the light ends column. Accordingly, the light ends column overhead is treated with an amine compound (such as hydroxylamine), which reacts with the carbonyl compounds to form oxime derivatives that can be separated from the remaining overhead by distillation, resulting in an acetic acid product with improved permanganate time.

European Patent Application No. EP 0 687 662 A2 and U.S. Pat. No. 5,625,095 describe a process for producing high purity acetic acid in which it is stated that an acetaldehyde concentration of 400 ppm or less is maintained in the reactor by using a single or multi-stage distillation process to remove acetaldehyde. Streams suggested for processing to remove acetaldehyde include a light phase containing primarily water, acetic acid and methyl acetate; a heavy phase containing primarily methyl iodide, methyl acetate and acetic acid; an overhead stream containing primarily methyl iodide and methyl acetate; or a recirculating stream formed by combining the light and heavy phase. These references do not identify which of these streams possesses the greatest concentration of acetaldehyde.

EP 0 687 662 A2 and U.S. Pat. No. 5,625,095 also disclose management of reaction conditions to control the formation of acetaldehyde in the reactor. Although it is stated that formation of by-products such as crotonaldehyde, 2-ethylcrotonaldehyde, and alkyl iodides is reduced by controlling the formation of acetaldehyde, it is also pointed out that management of reaction conditions as proposed increases the formation of propionic acid, an undesirable by-product.

More recently, it has been disclosed in commonly assigned U.S. Pat. Nos. 6,143,930 and 6,339,171 that it is possible to significantly reduce the undesirable impurities in the acetic acid product by performing a multi-stage purification on the light ends column overhead. These patents disclose a purification process in which the light ends overhead is distilled twice, in each case taking the acetaldehyde overhead and returning a methyl iodide rich residuum to the reactor. The acetaldehyde-rich distillate is optionally extracted with water to remove the majority of the acetaldehyde for disposal, leaving a significantly lower acetaldehyde concentration in the raffinate that is recycled to the reactor. U.S. Pat. Nos. 6,143,930 and 6,339,171 are incorporated herein by reference in their entirety.

While the above-described processes have been successful in removing carbonyl impurities from the carbonylation system and for the most part controlling acetaldehyde levels and permanganate time problems in the final acetic acid product, further improvements can still be made. Accordingly, there remains a need for alternative processes to improve the efficiency of acetaldehyde removal. The present invention provides one such alternative solution.

SUMMARY OF INVENTION

In one aspect, the present invention provides a process for producing acetic acid that includes the following steps: (a) reacting methanol, methyl acetate, methyl formate or dimethyl ether with carbon monoxide in a suitable reaction medium that includes a catalyst and an organic iodide; (b) separating the products of the reaction into a volatile product phase that contains acetic acid, methyl iodide, water, and permanganate reducing compounds (PRC's), and a less volatile phase containing the catalyst and acetic acid; (c) distilling the volatile product phase to yield a purified product and a first overhead that contains organic iodide, water, acetic acid, and unreacted methanol; (d) distilling at least a portion of the first overhead to produce a second overhead containing methyl iodide, water, $C_{2-12}$ alkyl iodides, PRC's and dimethyl ether; (e) extracting the second overhead with water to provide a first aqueous extract and a first raffinate; and (f) extracting the first raffinate with water to provide a second raffinate and a second aqueous extract containing concentrated PRC's for disposal.

Preferably, at least a portion of the second raffinate is recycled directly or indirectly to the reactor, as are the bottoms from the distillation steps. Most preferably, the second overhead contains sufficient dimethyl ether to reduce the solubility of methyl iodide in the aqueous extracts, as will be explained further below.

In another aspect, the present invention provides an improved method for separating a mixture containing water, acetic acid, methyl iodide, methyl acetate, methanol, at least one $C_{2-12}$ alkyl iodide and at least one permanganate reducing compound (PRC). The improved method includes the following steps: (a) distilling the mixture to form a PRC enriched overhead stream containing dimethyl ether; (b) extracting the overhead stream with water and separating therefrom a first aqueous stream containing at least one PRC; and (c) extracting the extracted overhead stream with water and separating therefrom a second aqueous stream containing at least one PRC. Most preferably, the overhead stream contains sufficient dimethyl ether to reduce the solubility of methyl iodide in the aqueous extracts.

In still another aspect, the present invention provides an improved method for reduction and/or removal of permanganate-reducing compounds (PRC's) and $C_{2-12}$ alkyl iodide compounds formed in the carbonylation of a carbonylatable material such as methanol, methyl acetate, methyl formate or dimethyl ether to a product of acetic acid. In the improved method, the methanol is carbonylated in a reaction medium containing a catalyst and an organic iodide; the products of the carbonylation reaction are phase separated into (1) a volatile phase containing acetic acid product, organic iodide, water, and at least one PRC, and (2) a less volatile phase; and the volatile phase is distilled to yield a purified product and an overhead containing organic iodide, water, acetic acid, and PRC. The improvement includes the steps of (a) distilling at least a portion of the overhead to provide a PRC enriched overhead stream containing dimethyl ether; (b) extracting the PRC enriched overhead stream with water and separating therefrom an aqueous waste stream containing PRC's; and (c) extracting the extracted overhead stream with water and separating therefrom a second aqueous waste stream also containing at least one PRC. Most preferably, the overhead stream contains sufficient dimethyl ether to reduce the solubility of methyl iodide in the aqueous extracts.

Figure 1:
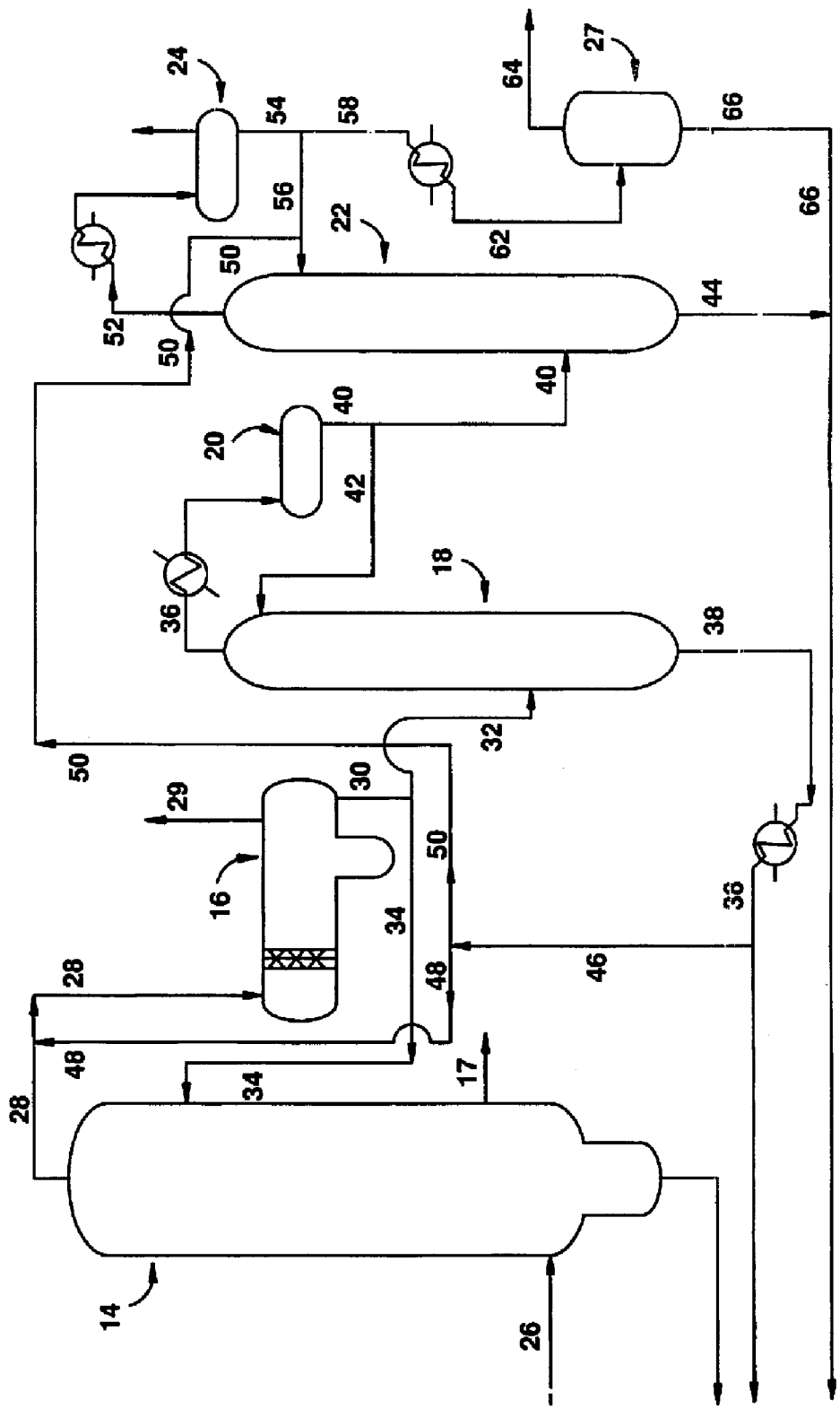
FIG. 1 illustrates the prior art process, as disclosed in U.S. Pat. No. 6,339,171, for the removal of carbonyl impurities from an intermediate stream of the carbonylation process for the production of acetic acid by a carbonylation reaction.
Figure 2:
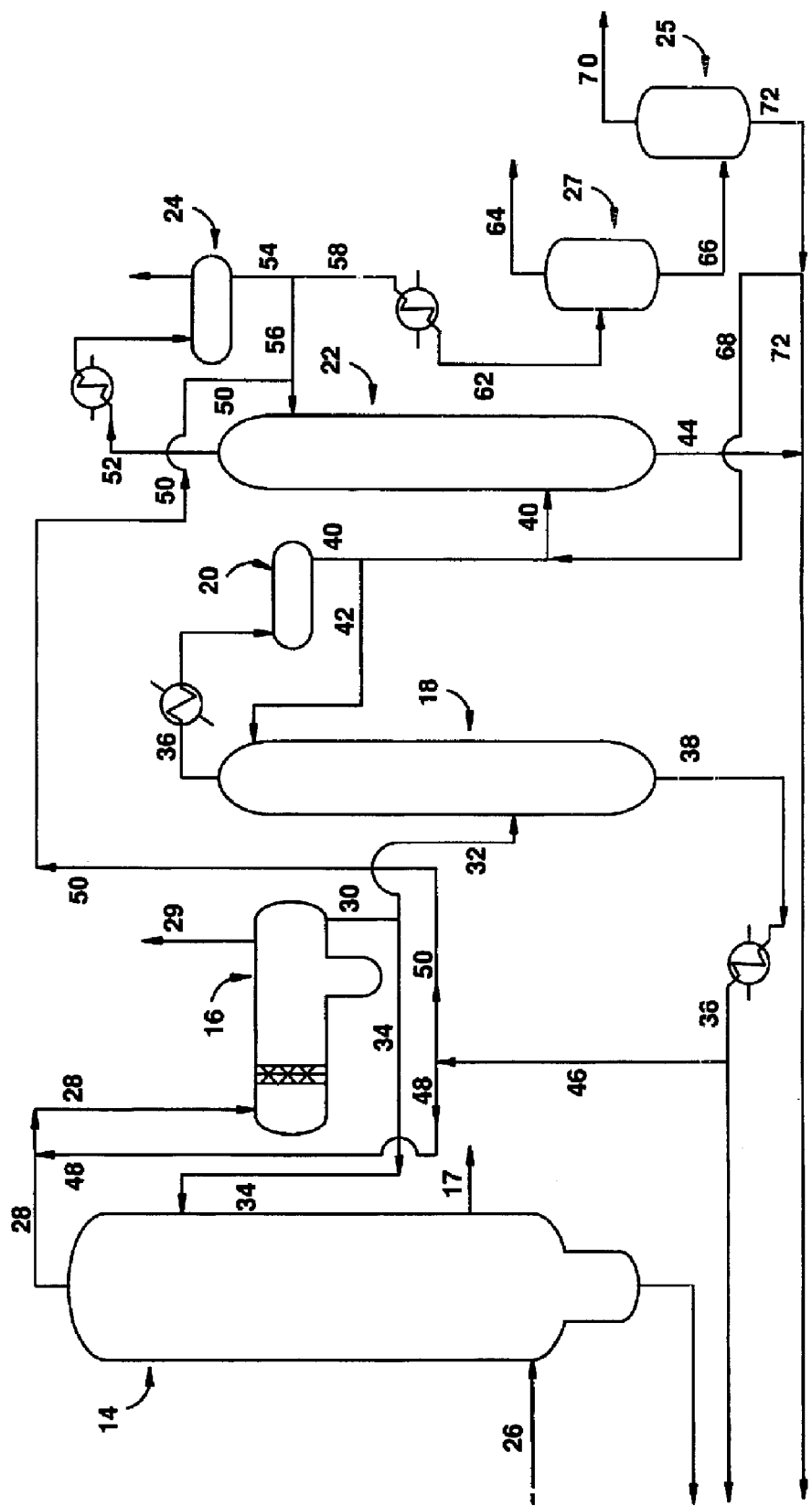
FIG. 2 illustrates a preferred embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents and alternatives falling within the scope of the invention as defined by the appended claims.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification process of the present invention is useful in any process used to carbonylate methanol (or another carbonylatable material such as methyl acetate, methyl formate or dimethyl ether, or mixtures thereof) to acetic acid in the presence of a Group VIII metal catalyst such as rhodium and an iodide promoter. A particularly useful process is the low water rhodium-catalyzed carbonylation of methanol to acetic acid as exemplified in U.S. Pat. No. 5,001,259. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, etc., or other coordination compounds of rhodium, and the like.

The halogen-promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol, which is carbonylated. Thus, in the carbonylation of methanol to acetic acid, the halide promoter will include methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process is the carboxylic acid product. Thus, in the carbonylation of methanol to acetic acid, the preferred solvent is acetic acid.

Water is contained in the reaction medium but at concentrations well below that which has heretofore been thought practical for achieving sufficient reaction rates. It has previously been taught that in rhodium-catalyzed carbonylation reactions of the type set forth in this invention, the addition of water exerts a beneficial effect upon the reaction rate (U.S. Pat. No. 3,769,329). Thus most commercial operations run at water concentrations of at least about 14 wt %. Accordingly, it is quite unexpected that reaction rates substantially equal to and above reaction rates obtained with such high levels of water concentration can be achieved with water concentrations below 14 wt % and as low as about 0.1 wt %.

In accordance with the carbonylation process most useful to manufacture acetic acid according to the present invention, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously (U.S. Pat. No. 5,001,259). The concentration of lithium iodide used in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed, which is in the liquid phase, with gaseous carbon monoxide bubbled through a liquid acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be used provided that the salt is sufficiently soluble in the reaction medium to provide the desired level of the iodide. When the iodide is added as a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being preferred. In the low water carbonylation process most useful in this invention, the additional iodide over and above the organic iodide promoter is present in the catalyst solution in amounts of from about 2 to about 20 wt %, the methyl acetate is present in amounts of from about 0.5 to about 30 wt %, and the lithium iodide is present in amounts of from about 5 to about 20 wt %. The rhodium catalyst is present in amounts of from about 200 to about 2000 parts per million (ppm).

Typical reaction temperatures for carbonylation will be approximately 150 to about 250° C., with the temperature range of about 180 to about 220° C. being the preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

A typical reaction and acetic acid recovery system that is used for the iodide-promoted rhodium catalyzed carbonylation of methanol to acetic acid is shown in FIG. 1 and includes a liquid phase carbonylation reactor, flasher, and a methyl iodide acetic acid light ends column 14 which has an acetic acid side stream 17 which proceeds to further purification. The reactor and flasher are not shown in FIG. 1. These are considered standard equipment now well known in the carbonylation process art. The carbonylation reactor is typically either a stirred vessel or bubble-column type within which the reacting liquid or slurry contents are maintained automatically at a constant level. Into this reactor there are continuously introduced fresh methanol, carbon monoxide, sufficient water as needed to maintain at least a finite concentration of water in the reaction medium, recycled catalyst solution from the flasher base, a recycled methyl iodide and methyl acetate phase, and a recycled aqueous acetic acid phase from an overhead receiver decanter of the methyl iodide acetic acid light ends or splitter column 14. Distillation systems are employed that provide means for recovering the crude acetic acid and recycling catalyst solution, methyl iodide, and methyl acetate to the reactor. In a preferred process, carbon monoxide is continuously introduced into the carbonylation reactor just below the agitator, which is used to stir the contents. The gaseous feed is thoroughly dispersed through the reacting liquid by this stirring means. A gaseous purge stream is vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher the catalyst solution is withdrawn as a base stream (predominantly acetic acid containing the rhodium and the iodide salt along with lesser quantities of methyl acetate, methyl iodide, and water), while the vapor overhead stream of the flasher contains largely the product acetic acid along with methyl iodide, methyl acetate, and water. Dissolved gases exiting the reactor and entering the flasher consist of a portion of the carbon monoxide along with gaseous by products such as methane, hydrogen, and carbon dioxide and exit the flasher as part of the overhead stream. The overhead stream is directed to the light ends or splitter column 14 as stream 26.

It has been disclosed in U.S. Pat. Nos. 6,143,930 and 6,339,171 that there is a higher concentration, about 3 times, of the PRC's and in particular acetaldehyde content in the light phase than in the heavy phase stream exiting column 14. Thus, in accordance with the present invention, stream 28, containing PRC's is directed to an overhead receiver decanter 16 where the light ends phase, stream 30, is directed to distillation column 18.

The present invention may broadly be considered as an improved process for distilling PRC's, primarily aldehydes and alkyl iodides, from a vapor phase acetic acid stream, such as the overhead from a light ends distillation column or a combined light-ends/drying column. The vapor phase stream is distilled and then twice extracted to remove PRC's. An especially preferred method of removing aldehydes and alkyl iodides from a first vapor phase acetic acid stream, and reducing levels of propionic acid in the product, includes the following steps: a) condensing the first vapor phase acetic acid stream in a first condenser and biphasically separating it to form a first heavy liquid phase product and a first light liquid phase product; b) distilling the first light liquid phase product in a first distillation column to form a second vapor phase acetic acid product stream which is enriched with aldehydes and alkyl iodides with respect to said first vapor phase acetic acid stream; c) condensing the second vapor phase stream in a second condenser to form a second liquid phase product; d) distilling the second liquid phase product in a second distillation column to form a third vapor phase stream; e) condensing the third vapor phase stream and extracting the condensed stream with water to remove residual acetaldehyde therefrom; and f) extracting the extracted condensed stream with water to remove additional residual acetaldehyde therefrom.

An embodiment of the prior art as disclosed in U.S. Pat. No. 6,339,171 is shown in FIG. 1. Referring to FIG. 1, the first vapor phase acetic acid stream (28) contains methyl iodide, methyl acetate, acetaldehyde and other carbonyl components. This stream is then condensed and separated (in vessel 16) to separate the heavy phase product containing the larger proportion of catalytic components—which is recirculated to the reactor (not shown in FIG. 1), and a light phase (30) containing acetaldehyde, water, and acetic acid.

Either phase of the light ends overhead may be subsequently distilled to remove the PRC's and primarily the acetaldehyde component of the stream, although it is preferred to remove PRC's from the light phase (30) because it has been found that the concentration of acetaldehyde is somewhat greater in that phase. In the embodiment depicted and described herein, the distillation is carried out in two stages; but it will be appreciated that the distillation may be performed in a single column as well. The light phase (30) is directed to column 18, which serves to form a second vapor phase (36) enriched in aldehydes and alkyl iodides with respect to stream 28. Stream 36 is condensed (vessel 20) to form a second liquid phase product. The second liquid phase (40) containing acetaldehyde, methyl iodide, methanol, and methyl acetate is directed to a second distillation column (22) wherein the acetaldehyde is separated from the other components. This inventive process has been found to reduce and/or remove at least 50% of the alkyl iodide impurities found in an acetic acid stream. It has also been shown that acetaldehyde and its derivatives is reduced and/or removed by at least 50%, most often greater than 60%. As a result, it is possible to keep the concentration of propionic acid in the acetic acid product below about 400 parts per million by weight, preferably below about 250 parts per million.

From the top of the light ends or splitter column 14, vapors are removed via stream 28, condensed, and directed to vessel 16. The vapors are chilled to a temperature sufficient to condense and separate the condensable methyl iodide, methyl acetate, acetaldehyde and other carbonyl components, and water into two phases. A portion of stream 28 includes noncondensable gases such as carbon dioxide, hydrogen, and the like and can be vented as shown in stream 29 on FIG. 1. Also leaving overhead receiver decanter 16, but not illustrated in FIG. 1, is the heavy phase of stream 28. Ordinarily this heavy phase is recirculated to the reactor, but a slip stream, generally a small amount, e.g., 25 vol. %, preferably less than about 20 vol. %, of the heavy phase may also be directed to a carbonyl treatment process and the remainder recycled to the reactor or reaction system. This slip stream of the heavy phase may be treated individually or combined with the light phase (stream 30) for further distillation and extraction of carbonyl impurities.

The light phase (stream 30) is directed to distillation column 18. A portion of stream 30 is directed back to the light ends column 14 as reflux stream 34. The remainder of stream 30 enters column 18 as stream 32 in about the middle of the column. Column 18 serves to concentrate the aldehyde components of stream 32 into overhead stream 36 by separating water and acetic acid from the lighter components. First distillation column 18 preferably contains approximately 40 trays, and temperature ranges therein from about 283° F. (139.4° C.) at the bottom to about 191° F. (88.3° C.) at the top of the column. Exiting the bottom of 18 is stream 38 containing approximately 70% water and 30% acetic acid. Stream 38 is processed, generally cooled utilizing a heat exchanger, is recycled to the light ends column overhead decanter 16 via streams 46, 48 and ultimately to the reactor or reaction system. It has been found that recycling a portion of stream 38 identified as stream 46 back through decanter 16 increases efficiency of the inventive process and allows for more acetaldehyde to be present in the light phase, stream 32. Stream 36 has been found to have approximately seven times more aldehyde content when stream 38 is recycled through decanter 16 in this manner. Exiting the top of column 18 is stream 36 containing PRC's and in particular acetaldehyde, methyl iodide, methyl acetate, and methanol, and alkyl iodides. Stream 36 is then directed to an overhead receiver 20 after it has been chilled to condense any condensable gases present.

Exiting overhead receiver 20 is stream 40 containing acetaldehyde, methyl iodide, methyl acetate, and methanol. A portion of stream 40 is returned to column 18 as reflux stream 42. The remainder of stream 40 enters second distillation column 22 close to the bottom of the column. Column 22 serves to separate the majority of the acetaldehyde from the methyl iodide, methyl acetate, and methanol in stream 40. In one embodiment, column 22 contains about 100 trays and is operated at a temperature ranging from about 224° F. (106.6° C.) at the bottom to about 175° F. (79.4° C.) at the top. In an alternate, preferred embodiment, column 22 contains structured packing in place of trays. The preferred packing is a structured packing with an interfacial area of about 65 $ft^2/ft^3$, preferably made from a metallic alloy like 2205 or other like packing material, provided it is compatible with the compositions to be purified in the column. It was observed during experimentation that uniform column loading, which is required for good separation, was better with structured packing than with trays. Alternatively, ceramic packing may be employed. The residue of column 22, stream 44, exits at the bottom of the column and is recycled to the carbonylation process.

Acetaldehyde polymerizes in the presence of methyl iodide to form metaldehyde and paraldehyde. These polymers generally are low molecular weight, less than about 200. Paraldehyde has been found to be relatively soluble in the reaction liquid, and primarily in acetic acid. Metaldehyde, upon its precipitation, is a sand-like, granular polymer that is not soluble in the reaction liquid beyond about 3 wt % concentration.

As disclosed in U.S. Pat. No. 6,339,171, however, it has been discovered that during the reaction, and with the heating of column 22, higher molecular weight polymers of acetaldehyde form. These higher molecular weight polymers (molecular weight greater than about 1000) are believed to form during processing of the light phase and are viscous and thixotropic. As heat is applied to the system, they tend to harden and adhere to the walls of the tower where their removal is cumbersome. Once polymerized, they are only slightly soluble in organic or aqueous solvents and can be removed from the system only by mechanical means. Thus an inhibitor is needed, preferably in column 22, to reduce the formation of these impurities, i.e., metaldehyde and paraldehyde and higher molecular weight polymers of acetaldehyde (AcH). Inhibitors generally consist of $C_{1-10}$ alkanols, preferably methanol; water; acetic acid and the like used individually or in combination with each other or with one or more other inhibitors. Stream 46, which is a portion of column 18 residue and a slip stream of stream 38, contains water and acetic acid and hence can serve as an inhibitor. As shown in FIG. 1, stream 46 splits to form streams 48 and 50. Stream 50 is added to column 22 to inhibit formation of metaldehyde and paraldehyde impurities and higher molecular weight polymers. Since the residue of second column 22 is recycled to the reactor, any inhibitors added must be compatible with the reaction chemistry. It has been found that small amounts of water, methanol, acetic acid, or a combination thereof, do not interfere with the reaction chemistry and practically eliminate the formation of polymers of acetaldehyde. Stream 50 is also preferably employed as an inhibitor since this material does not change the reactor water balance. Although water is not particularly preferred as an inhibitor, other important advantages are obtained by adding water to column 22 as will be explained below.

Exiting the top of column 22 is stream 52 containing PRC's. Stream 52 is directed to a condenser and then to overhead receiver 24. After condensation, any noncondensable materials are vented from receiver 24; the condensed materials exit receiver 24 as stream 54. Stream 56, a slip stream of stream 54, is used as reflux for column 22. Exiting the bottom of column 22 is stream 44 containing methyl iodide, methanol, methyl acetate, methanol and water. This stream is combined with stream 72, which will be described below, and directed to the reactor.

It is important for the extraction mechanism that the overhead stream of column 22 remain cold, generally at a temperature of about 13° C. This stream may be obtained or maintained at about 13° C. by conventional techniques known to those of skill in the art, or any mechanism generally accepted by the industry.

Upon exiting receiver 24, stream 58 is preferably sent through a condenser/chiller (now stream 62) and then to a first extractor 27. In extractor 27, PRC's and alkyl iodides are extracted with water, preferably water from an internal stream so as to maintain water balance within the reaction system. As a result of this extraction, methyl iodide separates from the aqueous PRC's and alkyl iodide phase. In a preferred embodiment, a mixer-settler with a water-to-feed ratio of about 2 is employed.

The aqueous extract stream 64 leaves the extractor 27 from the top thereof. This PRC-rich, and in particular, acetaldehyde-rich aqueous phase is directed to waste treatment. Also exiting the extractor is raffinate stream 66 containing methyl iodide.

Raffinate stream 66 is extracted with additional water in a second extractor 25. In extractor 25, as in extractor 27, PRC's and alkyl iodides are extracted with water, preferably water from an internal stream so as to maintain water balance within the reaction system. As a result of this extraction, methyl iodide separates from the aqueous PRC's and alkyl iodide phase. In a preferred embodiment, a mixer-settler with a water-to-feed ratio of about 1 is employed. The aqueous extract stream 70 leaves the extractor from the top thereof. This PRC-rich, and in particular, acetaldehyde-rich aqueous phase is directed to waste treatment. Also exiting the extractor is raffinate stream 72 containing methyl iodide. This stream is normally recycled to the reaction system and ultimately to the reactor.

It will be immediately apparent to one of ordinary skill in the art that additional extraction stages may be added as desired to further increase the fraction of methyl iodide recovered from the acetaldehyde-rich overhead from column 22. It will also be apparent that additional variations are possible in which a single water stream passes through the extraction stages in series rather than using fresh water in each stage. Finally, it will be apparent that the multistage extraction as described herein may also be accomplished using a packed-bed (continuous contacting) extractor having a suitable number of theoretical stages in place of equipment having discrete stages.

One potential problem with the multistage extraction described hereinabove is that each water extraction removes not only acetaldehyde but also a measurable amount of methyl iodide. As explained hereinabove, because methyl iodide is an especially costly component of the reaction system, it is highly desirable to minimize the amount of methyl iodide that is removed from the process as waste so as to reduce the quantity of fresh methyl iodide that must be fed to the reactor. The present applicants have discovered, however, that adding dimethyl ether (DME) to the feed to extractor 27 limits the loss of methyl iodide in the extraction steps. The presence of DME reduces the solubility of methyl iodide in water, thereby reducing the amount of methyl iodide extracted into aqueous extract streams 64 and 70 and lost in wastewater treatment. By way of example, the applicants observed that the concentration of methyl iodide in stream 64 dropped from about 1.8% when no DME was present to about 0.5% when DME was present. Accordingly, a further aspect of the present invention includes the step of injecting DME into the process upstream of extractor 27, for example into stream 62, to reduce the loss of methyl iodide into the aqueous extract streams 64 and 70. The required quantity of DME in stream 62 can be obtained by adding water to column 22, for example to the feed 40 or reflux 50. Although one need not understand the precise mechanism of DME formation in column 22 to practice the present invention, it is believed that this water reacts with methyl acetate and/or methyl iodide in column 22 to form methanol, which is then dehydrated in the presence of an acid catalyst (such as HI) to form DME. Any DME that is not extracted into the aqueous extract streams 64 and 70 is recycled directly or indirectly to the reaction system, where it reacts with carbon monoxide and water to form acetic acid.

While the invention has been described with reference to the preferred embodiments, obvious modifications and alterations are possible by those skilled in the related art. In particular, although the present invention has been generally described above utilizing the light ends phase of column 14, any stream in the carbonylation process having a high concentration of PRC's and alkyl iodides may be treated in accordance with the present invention. Therefore, it is intended that the invention include all such modifications and alterations to the full extent that they come within the scope of the following claims or the equivalents thereof.

The invention claimed is:

1. An improved method for reduction and/or removal of permanganate-reducing compounds (PRC's), $C_{3-8}$ carboxylic acids and $C_{2-12}$ alkyl iodide compounds formed in the carbonylation of a carbonylatable reactant selected from the group consisting of methanol, methyl acetate, methyl formate and dimethyl ether and mixtures thereof to an acetic acid product, the products of said carbonylation including a volatile chase that is distilled to yield a purified acetic acid product and a first overhead comprising methyl iodide, water and at least one PRC, wherein the improvement comprises the steps of:
   (a) distilling at least a portion of the first overhead to produce a second overhead stream comprising methyl iodide, dimethyl ether, and said at least one PRC;
   (b) extracting the second overhead stream with water to form a first raffinate and a first aqueous extract stream containing said at least one PRC; and
   (c) extracting the first raffinate with water to form a second raffinate and a second aqueous extract stream containing said at least one PRC,
   wherein the improvement further comprises introducing at least a portion of the second raffinate directly or indirectly into the reaction medium.

2. An improved method for reduction and/or removal of permanganate-reducing compounds (PRC's), $C_{3-8}$ carboxylic acids and $C_{2-12}$ alkyl iodide compounds formed in the carbonylation of a carbonylatable reactant selected from the group consisting of methanol, methyl acetate, methyl formate and dimethyl ether and mixtures thereof to an acetic acid product, the products of said carbonylation including a volatile phase that is distilled to yield a purified acetic acid product and a first overhead comprising methyl iodide, water and at least one PRC, wherein the improvement comprises the steps of:
   (a) distilling at least a portion of the first overhead to produce a second overhead stream comprising methyl iodide, dimethyl ether, and said at least one PRC;
   (b) extracting the second overhead stream with water to form a first raffinate and a first aqueous extract stream containing said at least one PRC; and
   (c) extracting the first raffinate with water to form a second raffinate and a second aqueous extract stream containing said at least one PRC,
   wherein water for one of extraction steps (b) and (c) comprises at least a portion of one of the aqueous extract streams.

3. An improved method for reduction and/or removal of permanganate-reducing compounds (PRC's), $C_{3-8}$ carboxylic acids and $C_{2-12}$ alkyl iodide compounds formed in the carbonylation of a carbonylatable reactant selected from the group consisting of methanol, methyl acetate, methyl formate and dimethyl ether and mixtures thereof to an acetic acid product, the products of said carbonylation including a volatile phase that is distilled to yield a purified acetic acid product and a first overhead comprising methyl iodide, water and at least one PRC, wherein the improvement comprises the steps of:
   (a) distilling at least a portion of the first overhead to produce a second overhead stream comprising methyl iodide, dimethyl ether, and said at least one PRC;
   (b) extracting the second overhead stream with water to form a first raffinate and a first aqueous extract stream containing said at least one PRC; and (c) extracting the first raffinate with water to form a second raffinate and a second aqueous extract stream containing said at least one PRC, further comprising the step of adding dimethyl ether to at least one stream associated with said distillation step (a).

4. A process for producing acetic acid, comprising the steps of:
(a) carbonylating at least one reactant selected from the group consisting of methanol, methyl acetate, methyl formate and dimethyl ether in a reactor containing a suitable reaction medium comprising an organic iodide;
(b) separating the products of said carbonylation into a volatile product phase comprising acetic acid, and a less volatile phase;
(c) distilling said volatile product phase to yield a purified acetic acid product and a first overhead comprising said organic iodide and at least one permanganate reducing compound (PRC);
(d) distilling at least a portion of the first overhead to produce a PRC-enriched second overhead, said second overhead further comprising dimethyl ether; and
(e) extracting the second overhead with water,
wherein step (e) comprises at least two consecutive extraction steps, each extraction step comprising contacting the second overhead with water and separating therefrom an aqueous stream comprising said at least one PRC,
further comprising recycling at least a portion of the extracted second overhead directly or indirectly to the reactor.

5. A process for producing acetic acid, comprising the steps of:
(a) carbonylating at least one reactant selected from the group consisting of methanol, methyl acetate, methyl formate and dimethyl ether in a reactor containing a suitable reaction medium comprising an organic iodide;
(b) separating the products of said carbonylation into a volatile product phase comprising acetic acid, and a less volatile phase;
(c) distilling said volatile product phase to yield a purified acetic acid product and a first overhead comprising said organic iodide and at least one permanganate reducing compound (PRC);
(d) distilling at least a portion of the first overhead to produce a PRC-enriched second overhead, said second overhead further comprising dimethyl ether; and
(e) extracting the second overhead with water,
wherein step (e) comprises at least two consecutive extraction steps, each extraction step comprising contacting the second overhead with water and separating therefrom an aqueous stream comprising said at least one PRC, further comprising the step of adding dimethyl ether to at least one stream associated with said distillation step (d).

6. A process for separating a mixture comprising water, acetic acid, methyl iodide, methyl acetate, methanol, and at least one permanganate reducing compound (PRC), said process comprising the steps of:
(a) distilling the mixture to separate the mixture into a plurality of streams, at least one of said streams being a PRC enriched overhead stream comprising dimethyl ether; and
(b) extracting the PRC enriched overhead stream with water,
wherein step (b) comprises at least two consecutive extraction steps, each extraction step comprising contacting the PRC enriched overhead stream with water and separating therefrom an aqueous stream comprising said at least one PRC,
further comprising the step of adding dimethyl ether to the PRC enriched overhead stream before extracting the PRC enriched overhead stream with water.

7. A process for separating a mixture comprising water, acetic acid, methyl iodide, methyl acetate, methanol, and at least one permanganate reducing compound (PRC), said process comprising the steps of:
(a) distilling the mixture to separate the mixture into a plurality of streams, at least one of said streams being a PRC enriched overhead stream comprising dimethyl ether;
(b) extracting the PRC enriched overhead stream with water, wherein step (b) comprises at least two consecutive extraction steps, each extraction step comprising contacting the PRC enriched overhead stream with water and separating therefrom an aqueous stream comprising said at least one PRC;
(c) performing a liquid-vapor chase separation on the effluent of a methanol carbonylation reactor to form a vapor phase and a liquid phase;
(d) distilling the vapor phase to form a first overhead and a liquid product; and
(e) condensing at least a portion of the first overhead to provide said liquid composition,
further comprising recycling at least a portion of the extracted PRC enriched overhead directly or indirectly to the reactor.

* * * * *